(12) United States Patent
Katada et al.

(10) Patent No.: US 7,888,002 B2
(45) Date of Patent: Feb. 15, 2011

(54) METHOD FOR MIXING TWO OR MORE TYPES OF LIQUIDS IN POROUS CARRIERS

(75) Inventors: Junichi Katada, Kanagawa (JP); Akira Wakabayashi, Minami-Ashigara (JP)

(73) Assignee: Fujifilm Corporation, Tokyo (JP)

( * ) Notice: Subject to any disclaimer, the term of this patent is extended or adjusted under 35 U.S.C. 154(b) by 242 days.

(21) Appl. No.: 12/285,079

(22) Filed: Sep. 29, 2008

(65) Prior Publication Data

US 2009/0104715 A1    Apr. 23, 2009

(30) Foreign Application Priority Data

Sep. 28, 2007    (JP) .............................. 2007-254175

(51) Int. Cl.
*G01N 33/53*    (2006.01)
(52) U.S. Cl. ........................... 435/4; 435/7.1; 435/7.93; 435/7.94; 435/7.95; 435/287.1; 435/287.7; 435/287.8; 435/287.9; 435/288.2; 435/288.5; 422/100; 422/101; 422/56; 422/57; 422/60; 422/61
(58) Field of Classification Search ..................... 435/4, 435/7.1, 7.93, 7.94, 7.95, 287.1, 287.7, 287.8, 435/287.9, 288.2, 288.5; 436/514, 518, 808, 436/809, 810, 823; 322/102, 100, 101, 56, 322/57, 60, 61
See application file for complete search history.

(56) References Cited

U.S. PATENT DOCUMENTS

| | | | |
|---|---|---|---|
| 4,855,240 A | | 8/1989 | Rosenstein et al. |
| 4,960,691 A | * | 10/1990 | Gordon et al. .................. 435/6 |
| 5,238,652 A | * | 8/1993 | Sun et al. ....................... 422/61 |
| 5,308,775 A | * | 5/1994 | Donovan et al. ............. 436/518 |
| 6,017,494 A | | 1/2000 | Ashihara et al. |
| 7,270,995 B2 | * | 9/2007 | Matsushita et al. ......... 435/287.2 |
| 7,605,004 B2 | * | 10/2009 | Zhou .......................... 436/518 |

(Continued)

FOREIGN PATENT DOCUMENTS

EP    1 962 093 A1    8/2008

(Continued)

*Primary Examiner*—Bao-Thuy L Nguyen
(74) *Attorney, Agent, or Firm*—Birch, Stewart, Kolasch & Birch, LLP

(57) ABSTRACT

It is an object of the present invention to provide a method for simply mixing two or more types of liquids in a porous carrier. The present invention provides a method for mixing two or more types of liquids in a porous carrier, which comprises: laminating a first porous carrier consisting of an upstream portion and a down stream portion that are integrated with each other on a second porous carrier consisting of an upstream portion and a downstream portion that are integrated with each other, such that the upstream portion of the first porous carrier and the upstream portion of the second porous carrier form a bifurcated portion; adding a first liquid to the upstream portion of the first porous carrier; adding a second liquid to the upstream portion of the second porous carrier; and giving external force in a vertical direction towards the first and second porous carriers at a position wherein the first porous carrier is laminated on the second porous carrier on the side downstream of the bifurcation point of the bifurcated portion, so as to mix the first liquid with the second liquid in the first and second porous carriers.

4 Claims, 6 Drawing Sheets
(2 of 6 Drawing Sheet(s) Filed in Color)

(A)

(B)

(C)

U.S. PATENT DOCUMENTS 7,618,591 B2 * 11/2009 Slowey et al. ............... 422/102
7,648,829 B2 * 1/2010 Alderete et al. ............ 435/7.32

FOREIGN PATENT DOCUMENTS

| | | |
|---|---|---|
| JP | 10-104236 A | 4/1998 |
| JP | 2002-202307 A | 7/2002 |
| WO | WO-95/16207 A1 | 6/1995 |
| WO | WO-2006/098804 A2 | 9/2006 |

* cited by examiner

METHOD FOR MIXING TWO OR MORE TYPES OF LIQUIDS IN POROUS CARRIERS

TECHNICAL FIELD

The present invention relates to a method for mixing two or more types of liquids in a porous carrier.

BACKGROUND ART

As a method for qualitatively or quantitatively measuring a test substance existing in a biological sample such as urine or blood, immunoassay has been widely used. Among such immunoassay methods, an immunochromatography has been commonly used because it involves simple operations and it enables measurement in a short time. As a method for supplying two types of liquids to a membrane, the method described in JP Patent Publication (Kokai) No. 10-104236 A (1998) has been known.

At present, a common immunochromatography is problematic in that an antigen is not detected due to low sensitivity and the result becomes false negative. Thus, it is desired to develop an immunochromatography with a higher sensitivity. A silver amplification method has been known as a method for realizing a high sensitivity of an immunochromatography using a gold colloid as a labeling substance. According to JP Patent Publication (Kokai) No. 2002-202307 A, after a sample solution has been supplied, a solution used for silver amplification is added dropwise to a test line portion for amplification, so as to achieve a high sensitivity. However, in general, when such solutions used in silver amplification are mixed up, the mixed solution becomes extremely poor in terms of preservation quality. Thus, in the case of the silver amplification solution used in the silver amplification method described in JP Patent Publication (Kokai) No. 2002-202307 A, two types of liquids, which have been preserved separately, are mixed, and the thus mixed solution is then added dropwise to a test line portion, thereby performing silver amplification.

DISCLOSURE OF THE INVENTION

A silver amplification method has been known as a method for realizing a high sensitivity of an immunochromatography using a gold colloid as a labeling substance. In general, when solutions used in silver amplification are mixed up, the mixed solution becomes extremely poor in terms of preservation quality. Thus, a method of mixing two types of liquids, which have been preserved separately, and then adding the thus mixed solution dropwise to a test line portion, has been adopted. However, this method requires time and effort, and thus it cannot provide simplicity, a characteristic of the immunochromatography. It is an object of the present invention to overcome the aforementioned problem of the prior art technique. Namely, it is an object of the present invention to provide a method for simply mixing two or more types of liquids in a porous carrier.

As a result of intensive studies directed towards achieving the aforementioned object, the present inventors have found that a first porous membrane is laminated on a second porous membrane that differs from the first porous membrane such that one end of the first porous membrane and one end of the second porous membrane can form a bifurcated portion, and that two types of solutions are individually supplied through the two sections of the bifurcated portion, while external force is given to a portion on the side downstream of the bifurcation point of the second laminated porous membrane, so that the two types of liquids can be mixed in the porous membrane. In addition, the inventors have demonstrated that, by mixing two types of liquid in a porous membrane according to the aforementioned method, an assay can easily be carried out in an immunochromatography using a porous carrier for detecting a test substance, without mixing two types of liquids outside the test system. The present invention has been completed based on these findings.

Thus, the present invention provides a method for mixing two or more types of liquids in a porous carrier, which comprises: laminating a first porous carrier consisting of an upstream portion and a down stream portion that are integrated with each other on a second porous carrier consisting of an upstream portion and a downstream portion that are integrated with each other, such that the upstream portion of the first porous carrier and the upstream portion of the second porous carrier form a bifurcated portion; adding a first liquid to the upstream portion of the first porous carrier, adding a second liquid to the upstream portion of the second porous carrier; and giving external force in a vertical direction towards the first and second porous carriers at a position wherein the first porous carrier is laminated on the second porous carrier on the side downstream of the bifurcation point of the bifurcated portion, so as to mix the first liquid with the second liquid in the first and second porous carriers.

Preferably, the first porous carrier consists of an upstream portion and a downstream portion, and the upstream portion and the downstream portion are bent to form an integrated body, and the second porous carrier consists of an upstream portion and a downstream portion, and the upstream portion and the downstream portion are bent to form an integrated body.

Preferably, the method of the present invention is applied in an immunochromatography using a porous carrier for detecting a test substance.

Preferably, the method of the present invention is applied in a sandwich or competitive immunochromatography comprising developing a test substance and a labeling substance modified with a first binding substance reacting with the test substance on a porous carrier in a state where the test substance and the labeling substance is mixed, and capturing the test substance and the labeling substance at a reaction site on a porous carrier having a second binding substance reacting with the test substance or a substance binding with the first binding substance, so as to detect the test substance.

Preferably, the first binding substance is an antibody, and/or the second binding substance is an antibody.

Preferably, one of the first liquid and the second liquid contains any one of silver, silver ion and a silver compound, and the other of the first liquid and the second liquid contains a reducing agent.

According to the method of the present invention, the mixing of two or more types of liquids in a porous carrier can be achieved. In a silver amplification system, which has previously required the mixing of two types of liquids in two different places, the time and effort necessary for such mixing can be omitted, and two types of liquids can directly be applied to the test strip membrane of immunochromatography for silver amplification. That is, in the present invention, since two or more types of liquids can easily be mixed in a porous carrier, it becomes possible to mix solutions used for silver amplification in a porous membrane used in immunochromatography, for example. Thus, a simple, high-sensitive assay device, which does not require the time and effort for mixing liquids immediately before silver amplification and adding the mixed solution dropwise to the reaction system, can be achieved.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 10 shows the results of Example 2.
1: Back adhesive sheet
2: Gold colloid antibody-retaining pad
3: Antibody-immobilized membrane
3a: Capturing site
31: Detection portion
32: Control portion
4: Absorbent pad
5: Sample-adding pad
6: Sensitizing sheet
10: Immunochromatographic kit
11: Upstream portion
12: Upstream portion
21: Downstream portion
22 Downstream portion

BEST MODE FOR CARRYING OUT THE INVENTION

1. Method for Mixing Two or More Types of Liquids in Porous Carrier

Figure 1:
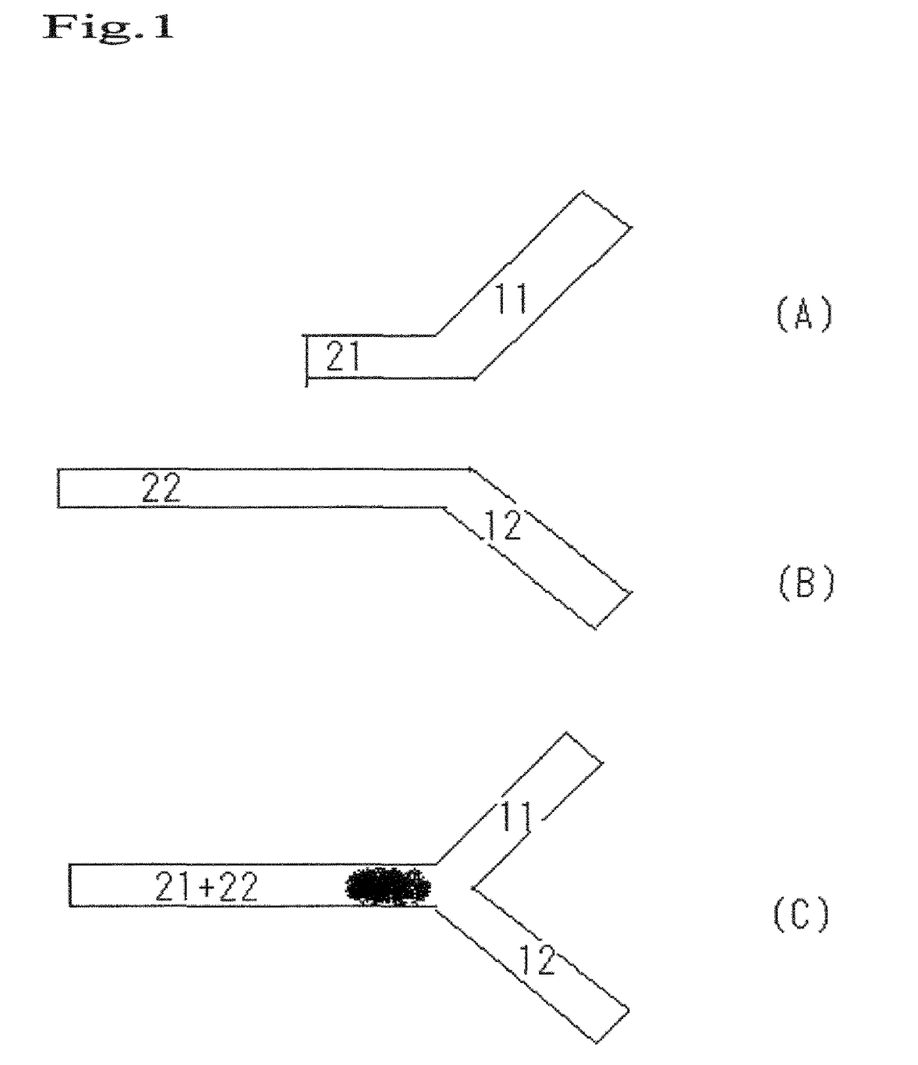
FIG. 1 shows an example of the form of a porous carrier used in the present invention.

In the present invention, a first porous carrier consisting of an upstream portion and a downstream portion that are integrated with each other and a second porous carrier consisting of an upstream portion and a downstream portion that are integrated with each other are used FIG. 1(A) shows an example of the first porous carrier consisting of an upstream portion and a downstream portion, wherein the upstream portion and the downstream portion are bent to form an integrated body. FIG. 1(B) shows an example of the second porous carrier consisting of an upstream portion and a downstream portion, wherein the upstream portion and the downstream portion are bent to form an integrated body. The terms "upstream portion" is used in the present invention to mean a region upstream of the flow of a liquid when the liquid is flown to a porous carrier, and the term "downstream portion" is used in the present invention to mean a region downstream of the flow of a liquid when the liquid is flown to a porous carrier.

Each of 11 of FIGS. 1(A) and 12 of FIG. 1(B) indicates an upstream portion. In FIG. 1(A), a liquid is added to the upstream portion 11 (preferably, to the end of the upstream portion 11), so that the liquid can flow towards a downstream portion 21. Similarly, in FIG. 1(B), a liquid is added to the upstream portion 12 (preferably, to the end of the upstream portion 12), so that the liquid can flow towards a downstream portion 22.

As stated above, in the first porous carrier and in the second porous carrier, a liquid flows from the upstream portion to the downstream portion. Thus, the upstream portion and the downstream portion are preferably bent at an angle that does not cause significant hindrance to the flow of the liquid. Such a flexion angle is preferably between 0-degree or more and less than 90-degree, and more preferably between 10-degree or more and 80-degree or less. (It is to be noted that the flexion angle is set at approximately 45-degree in FIGS. 1(A) and 1(B), but the flexion angle is not particularly limited thereto.)

As described below, the upstream portions of the first porous carrier and second porous carrier are preferably bent in a direction opposite to each other, such that the laminated portion 12 of the first porous carrier and second porous carrier can form a bifurcated portion.

In the present invention, the first porous carrier is first laminated on the second porous carrier such that the upstream portion of the first porous carrier and the upstream portion of the second porous carrier can form a bifurcated portion. Thereafter, a first liquid is added to the upstream portion of the first porous carrier, and a second liquid is then added to the upstream portion of the second porous carrier. FIG. 1(C) shows a state where the first porous carrier is laminated on the second porous carrier. In this state, the upstream portion 11 of the first porous carrier and the upstream portion 12 of the second porous carrier form a bifurcated portion. Moreover, the downstream portion 21 of the first porous carrier is laminated on the downstream portion 22 of the second porous carrier, one above the other.

In the present invention, external force is given in a vertical direction towards the first and second porous carriers at a position wherein the first porous carrier is laminated on the second porous carrier on the side downstream of the bifurcation point of the bifurcated portion, so as to mix the first liquid with the second liquid in the first and second porous carriers. An example of the position wherein the first porous carrier is laminated on the second porous carrier on the side downstream of the bifurcation point of the bifurcated portion may be a portion filled with black ink as shown in FIG. 1(C). A means for giving external force in a vertical direction towards the first and second porous carriers is not particularly limited, as long as it is able to narrow the flow channel composed of the porous carriers. Examples of such a means for giving external force include a means for gripping with a clip, a means for bearing down with a stick or the like, a means for bearing down with a projection, a means for transmitting force obtained by pressing with a finger or the like to the porous carriers, and a means for placing a product with a certain weight on the porous carriers.

2. Immunochromatography

In general, immunochromatography is a method for determining and/or measuring an analyte, simply, rapidly and specifically, by the following means. That is to say, a chromatographic carrier having at least one reaction site comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction site. At the aforementioned reaction site, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

The apparatus used to perform such an immunochromatography in the present invention is characterized in that it comprises a compound containing silver and a reducing agent for silver ion, and in that a signal is amplified by an amplification reaction using, as a core, a complex of the aforementioned analytical target and the aforementioned labeling substance used in detection binding to the aforementioned immobilizing reagent, so as to achieve high sensitivity. According to the present invention, a simple, rapid and highly sensitive immunochromatography can be carried out without requiring the supply of metal ion or a reducing agent solution for amplification from outside, which the conventional immunochromatography has required.

3. Test Sample

The type of a test sample that can be analyzed by the immunochromatography of the present invention is not particularly limited, as long as it may comprise an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

4. Pre-Treatment of Test Sample

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

5. Structure

Figure 2:
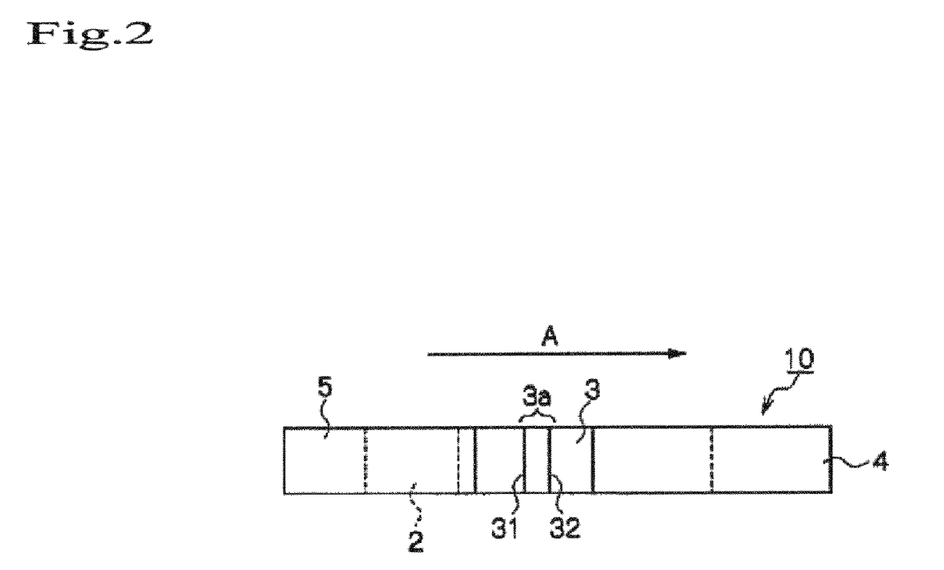
FIG. 2 is a plane view schematically showing an embodiment of an immunochromatographic kit
Figure 3:
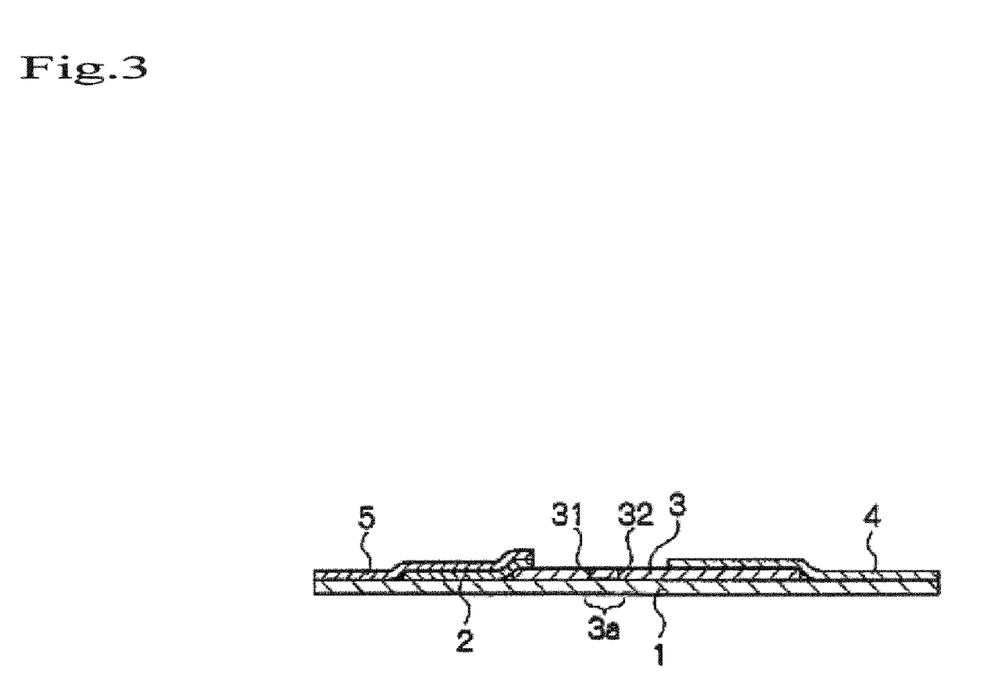
FIG. 3 is a longitudinal sectional view schematically showing a longitudinal section of the immunochromatographic kit as shown in FIG. 2.
Figure 4:
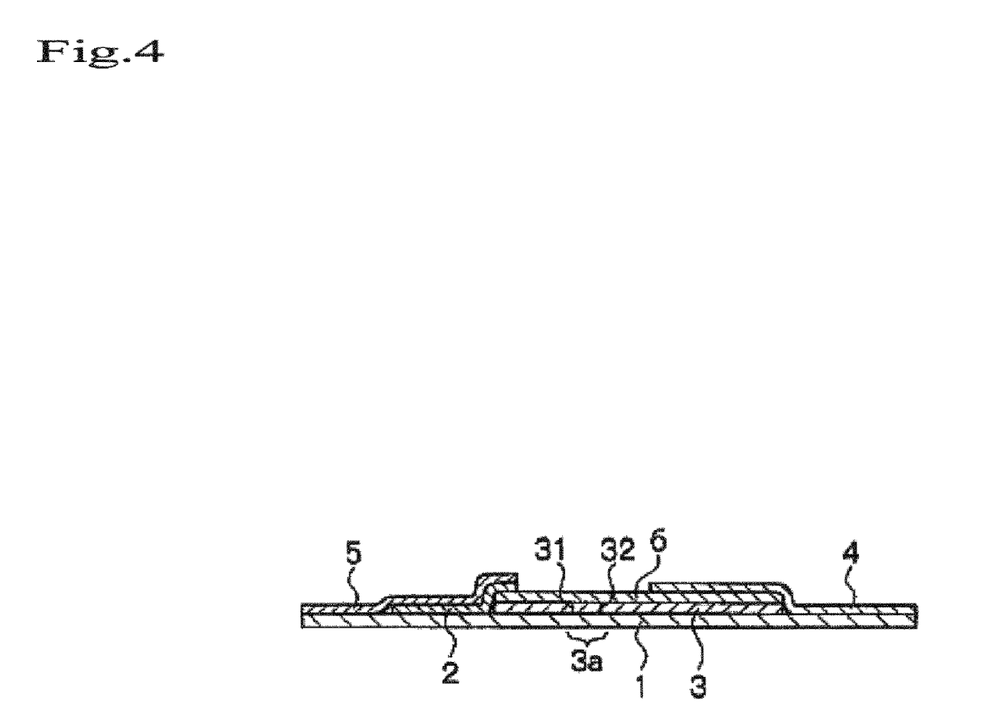
FIG. 4 is a longitudinal sectional view schematically showing a longitudinal section of another immunochromatographic kit that can be used in the present invention

The type of an immunochromatographic strip that can be used in the immunochromatography of the present invention is not particularly limited, as long as it is an immunochromatographic strip that can be used in a common immunochromatography. For example, FIG. 1 schematically shows a plane view of the conventional immunochromatographic strip, for example. FIG. 2 is a longitudinal sectional view schematically showing a longitudinal section of the immunochromatographic kit as shown in FIG. 1. FIG. 3 schematically shows a sectional view of another immunochromatographic strip.

In an immunochromatographic strip 10 of the present invention, a sample-adding pad 5, a labeling substance-retaining pad (e.g. a gold colloid antibody-retaining pad) 2, a chromatographic carrier (e.g. an antibody-immobilized membrane) 3, and an absorbent pad 4 are disposed in this order on an adhesive sheet 5 from the upstream to the downstream of a development direction (a direction indicated with the arrow A in FIG. 1).

The chromatographic carrier 3 has a capturing site 3a and a detection zone (which is also referred to as a "detection portion") 31 that is a region on which an antibody or an antigen specifically binding to an analytical target is immobilized. The chromatographic carrier 3 also has a control zone (which is also referred to as a "control portion") 32 that is a region on which a control antibody or antigen is immobilized, as desired. Further, the detection zone 31 and the control zone 32 comprise organic silver salts used for amplification and reducing agents used for silver ion.

The labeling substance-retaining pad 2 can be produced by preparing a suspension containing a labeling substance, applying the suspension to a suitable absorbent pad (e.g. a glass fiber pad), and then drying it.

As the sample-adding pad 1, a glass fiber pad can be used, for example.

5-1. Labeling Substance Used in Detection

As a labeling substance used in detection, a color particle used in immune agglutination can be used. For example, metals such as a metal colloid can be used. The mean particle diameter of a carrier particle (or colloid) is preferably between 0.02 and 10 μm. Liposomes or microcapsules containing pigments can also be used as such color particles. Conventionally known color metal colloids can all be used as such color particles for labeling. Examples of such color metal colloids include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 mm and 500 mm, more preferably between 1 nm and 50 nm, and particularly preferably between 1 nm and 15 nm.

Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

In the immunochromatography of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunochromatography of the present invention, one or more selected from these metal colloid labeling substances and/or metallic sulfide labeling substances may be used as a labeling substance(s).

5-2. Binding Substance

In the present invention, a labeling substance is modified with a first binding substance reacting with the test substance. The type of the first binding substance reacting with the test substance may be any substance so long as it has an affinity against the test substance. Examples of the first binding substance may include an antibody against the test substance (antigen), an antigen against the test substance (antibody), or an aptamer against the test substance (protein, low molecular weight compound, or the like), but are not limited thereto.

In the present invention, the porous carrier has (a) a second binding substance reacting with the test substance, or (b) a substance binding with the first binding substance. The type of the second binding substance reacting with the test substance may be any substance so long as it has an affinity against the test substance. Examples of the second binding substance may include an antibody against the test substance (antigen), an antigen against the test substance (antibody), or an aptamer against the test substance (protein, low molecular weight compound, or the like), but are not limited thereto. The second binding substance may be the same as or different from the first binding substance. Examples of the substance binding with the first binding substance may be the test substance, or a substance having a site which is recognized by the first binding substance, and may be a substance which is obtained by binding a derivative of the test substance with a protein (for example, BSA).

Preferably, the first binding substance is an antibody, and/or the second binding substance is an antibody. In the immunochromatography of the present invention, the type of an antibody having specificity for an analytical target is not particularly limited. Examples of an antibody used herein include an antiserum prepared from the serum of an animal immunized with the analytical target, an immunoglobulin fraction purified from the antiserum, a monoclonal antibody obtained by cell fusion using the splenic cells of the animal immunized with the analytical target, and the fragments thereof (for example, F(ab')$_2$, Fab, Fab' or Fv). Such an antibody may be prepared by a common method.

5-3. Chromatographic Carrier

The chromatographic carrier is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a substance used in detection is immobilized on a part of the chromatographic carrier to form a detection zone. The substance used in detection may be directly immobilized on a part of the chromatographic carrier via a physical or chemical bond. Alternatively, the substance used in detection may be bound physically or chemically to fine particles such as latex particles, and thereafter, the fine particles are immobilized on a part of the chromatographic carrier by trapping them thereon. After immobilization of the substance used in detection on the chromatographic carrier, the chromatographic carrier may preferably be subjected to a treatment for preventing unspecific adsorption, such as a treatment using an inert protein, and it may be then used.

5-4. Sample-Adding Pad

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

5-5. Labeling Substance-Retaining Pad

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it 5-6. Absorbent Pad The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

6. Immunological Test Method

Hereinafter, a sandwich method and a competitive method, which are specific embodiments of the immunochromatography of the present invention, will be described.

In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized second antibody, the analytical target (antigen) and the primary antibody, the labeled primary antibody that has not formed the aforementioned immune complex is removed. Subsequently, a metal ion and a reducing agent are supplied to a region of the insoluble thin-membrane support, on which the second antibody has been immobilized, for example, so that a signal from the labeling substance of the labeled primary antibody that has formed the aforementioned immune complex is amplified.

In the competitive method, an analytical target can be analyzed by the following procedures, for example, but the procedures are not particularly limited thereto. The competitive method is known as a means for detecting a low molecular weight antigen which can not be assayed in the sandwich method. First, a primary antibody having specificity for an analytical target (an antigen) has previously been prepared. In addition, the primary antibody has previously been labeled with metal colloid or the like. An analytical target, or a compound which has a site which is similar with that of the analytical target and has a same epitope against the primary antibody as that of the analytical target, both of which can bind to the primary antibody, is immobilized on a suitable insoluble thin-membrane support (e.g. a nitrocellulose membrane, a glass fiber membrane, a nylon membrane, a cellulose membrane, etc.). It is then allowed to come into contact with a test sample (or an extract thereof) that is likely to contain the analytical target (the antigen). If the analytical target does not exist in the test sample, an antigen-antibody reaction occurs on the insoluble support between the labeled primary antibody, and the analytical target, or the compound which has a same epitope against the primary antibody as that of the analytical target, both of which can bind to the primary antibody. If the analytical target exists in the test sample, the analytical target (antigen) binds to the labeled primary antibody, and thus an antigen-antibody reaction on the insoluble support between the labeled primary antibody, and the analytical target, or the compound which has a same epitope against the primary antibody as that of the analytical target, both of which can bind to the primary antibody, is inhibited. Namely, binding by the antigen-antibody reaction does not occur.

After completion of the reaction of the immobilized substance which can bind to the primary antibody and the labeled primary antibody, the labeled primary antibody that has not formed the aforementioned immune complex is removed. Subsequently, a metal ion and a reducing agent are supplied to a region of the insoluble thin-membrane support on which the substance which can bind to the primary antibody has been immobilized, for example, so that a signal from the labeling substance of the labeled primary antibody is amplified.

7. Amplification Solution

An amplification solution that can be used in the present invention is what is called a developing solution as described in publications common in the field of photographic chemistry (e.g. "*Kaitei Shashin kagaku no kiso, Ginen shashin hen* (Revised Basic Photographic Engineering, silver salt photography)," (the Society of Photographic Science and Technology of Japan, Colona Publishing Co., Ltd.); "*Shashin no kagaku* (Photographic Chemistry)," (Akira Sasasi, Shashin Kogyo Shuppan); "*Saishin Shoho Handbook* (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

8. Compound that Contains Silver

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotriazole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123,274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an α-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. No. 4,761,361 and No. 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt, etc.).

The inorganic silver salt used in the present invention is preferably a silver halide.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 µm or less, more preferably 0.10 µm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m$^2$, and preferably 0.01 to 0.05 mol/m$^2$, in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

9. Reducing Agent Used for Silver Ion

As a reducing agent used for silver ion, either inorganic or organic materials capable of reducing silver(I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent Useful ascorbic acid reducing agents include ascorbic acid, an analogue thereof an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376,510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis (hydroxyphenyl)methanes (that is, bisphenols), hindered phenols, and hindered naphthols, each of which may be substituted.

Typical binaphthols include, but are not limited to, 1,1'-bi-2-naphthol, 1,1'-bi-4-methyl-2-naphthol, and compounds described in U.S. Pat. Nos. 3,094,417 and 5,262,295.

Typical biphenols include, but are not limited to 2-(2-hydroxy-3-t-butyl-5-methylphenyl)-4-methyl-6-n-hexylphenol, 4,4'-dihydroxy-3,3',5,5'-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3,5-di-t-butyl-4-hydroxyphenyl)methane, 2,2'-bis(4-hydroxy-3-methylphenyl) propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, 2-methyl-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-β-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl) methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3-diones (for example, 2-phenylindane-1,3-dione), chromans (for example, 2,2-dimethyl-7-t-butyl-6-hydroxychroman), 1,4-dihydroxypyridines (for example, 2,6diethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents descried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt a substituted compound thereof or a mixture thereof with an ascorbic acid reducing agent used as a reducing agent.

The reducing agent of the present invention may be contained in an amount of 1 mass % to 10 mass % (dry mass) based on the amount of silver in organic silver. When the reducing agent is added to a layer other than the layer containing the organic silver salt in a multilayer structure, the amount of the reducing agent is slightly higher, and it is desirably from approximately 2 mass % to approximately 15 mass %. An auxiliary reducing agent is contained in an amount of about 0.001 mass % to 1.5 mass % (dry weight).

10. Other Auxiliary Agents

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof or tris(hydroxymethyl)aminomethane, and other buffers used in ordinary chemical experiments. Using these buffers as appropriate, the pH of the amplification solution can be adjusted to the optimal pH.

The present invention will be more specifically described in the following examples. However, these examples are not intended to limit the scope of the present invention

EXAMPLES

Test Example 1

Comparative Example 1

Figure 5:
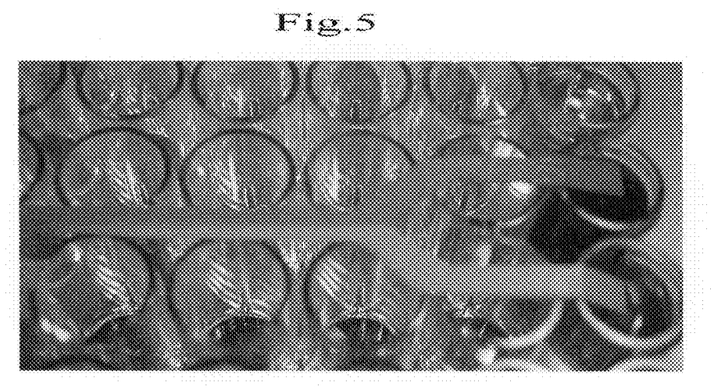
FIG. 5 shows the results of Comparative example 1.

A membrane manufactured by Whatman (Whatman QMA) was processed into a bifurcated portion. One section of the bifurcated portion was immersed in a solution colored with a blue pigment, and the other section was immersed in a solution colored with a red pigment. As a result, the solution penetrated into the portion due to capillary action. However, the solution became a laminar flow at the bifurcation point of the sections, and thus the two types of solutions were not mixed (FIG. 5).

Comparative Example 2

Figure 6:
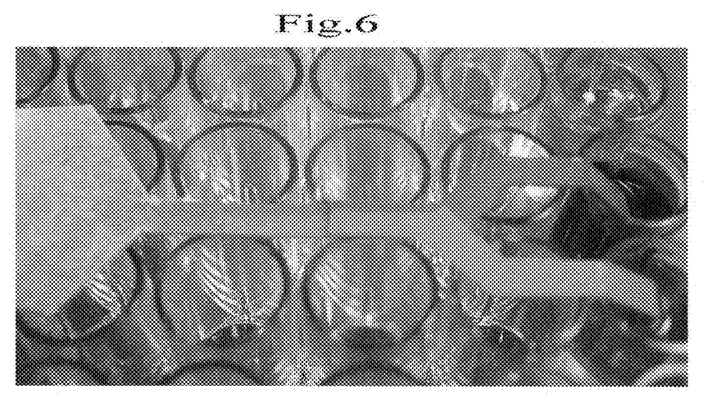
FIG. 6 shows the results of Comparative example 2.

As shown in FIG. 6, two membranes manufactured by Whatman (Whatman QMA) were laminated to form a bifurcated portion. One section of the bifurcated portion was immersed in a solution colored with a blue pigment, and the other section was immersed in a solution-colored with a red pigment. As a result, the solution penetrated into the portion due to capillary action. However, the solution became a laminar flow at the bifurcation point of the sections, and thus the two types of solutions were not mixed (FIG. 6).

Example 1

Figure 7:
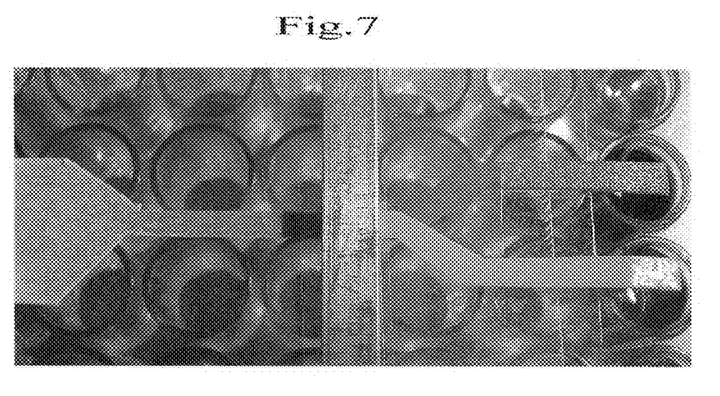
FIG. 7 shows the results of Example 1.

As shown in FIG. 7, two membranes manufactured by Whatman (Whatman QMA) were laminated to form a bifurcated portion, and pressure was given to the side downstream of the laminated portion. One section of the bifurcated portion was immersed in a solution colored with a blue pigment, and the other section was immersed in a solution colored with a red pigment. As a result, the solution penetrated into the portion due to capillary action. After the two solutions had passed the position at which the two sections met and the two membranes were laminated, they were mixed, and thus it was confirmed that the two solutions were blended (FIG. 7).

Test Example 2

(1) Preparation of Immunochromatography (1-1) Preparation of Anti-hCG Antibody Modified Gold Colloid Used as Labeling Substance in Detection 1 mL of a 50 mM $KH_2PO_4$ buffer (pH 7.0) was added to 9 mL of a solution of gold colloid (EM. GC50; manufactured by BBI) with a diameter of 50 nm, so as to adjust the pH. Thereafter, 1 mL of a solution of 50 μg/mL anti-hCG monoclonal antibody (Anti-hCG 5008 SP-5, manufactured by Medix Biochemica Co.) was added thereto, and the mixed solution was then stirred. The solution was left at rest for 10 minutes, and 550 μL of an aqueous solution of 1% polyethylene glycol (PEG—Mw: 20000; product number 168-11285; manufactured by Wako Pure Chemical Industries, Ltd.) was then added thereto, followed by stirring the mixed solution. Subsequently, 1.1 mL of an aqueous solution of 10% bovine serum albumin (BSA Fraction V; product number. A-7906; manufactured by Sigma) was added thereto, followed by stirring the mixed solution. This solution was centrifuged at 8000×g at 4° C. for 30 minutes (himac CF16RX; manufactured by Hitachi Ltd.), and the supernatant was then removed while approximately 1 mL remained. Thereafter, gold colloid was re-dispersed with an ultrasonic washer. Thereafter, the obtained dispersion was dispersed in 20 mL of a stock solution of gold colloid (20 mM Tris-HCl buffer (pH 8.2), containing 0.05% PEG (Mw: 20000), 150 mM NaCl, 1% BSA, and 0.1% $NaN_3$). The resultant dispersion was again centrifuged at 8000×g at 4° C. for 30 minutes, and the supernatant was then removed while approximately 1 mL remained. The gold colloid was re-dispersed with an ultrasonic washer, so as to obtain an antibody-modified gold colloid (50 nm) solution.

(1-2) Preparation of Gold Colloid Antibody-Retaining Pad

The antibody-modified gold colloid prepared in (1-1) above was diluted with water and a gold colloid coating solution (20 mM Tris-Hcl buffer (pH 8.2), containing 0.05% PEG (Mw: 20000) and 5% sucrose) such that the OD at 520 nm became 1.5. This solution was uniformly coated to glass fiber pads (Glass Fiber Conjugate Pad; manufactured by Millipore Corp.), each of which had been cut into a size of 8 mm×150 mm, in an amount of 0.8 mL per pad. The pads were dried under reduced pressure overnight, so as to obtain gold colloid antibody-retaining pads.

(1-3) Preparation of Antibody-Immobilized Membrane (Chromatographic Carrier)

The following method was applied to a nitrocellulose membrane (HiFlow Plus HF120 with a plastic lining; manufactured by Millipore Corp.) cut into a size of 25 mm×200 mm to immobilize an antibody thereon, thereby preparing an antibody-immobilized membrane. Using an inkjet-type coater (manufactured by BioDot Ltd.), a solution of an anti-hCG monoclonal antibody for immobilization (Anti-Alpha subunit 6601 SPR-5; manufactured by Medix Biochemica) prepared in a concentration of 0.5 mg/ml was applied to the membrane with one of its long sides directed downwards, at a position of 8 mm from the bottom, thereby forming a line shape with a width of approximately 1 mm. In a similar manner, a solution of a control anti-mouse IgG antibody (anti-mouse IgG (H+ L), rabbit F(ab')2; product No. 566-70621; manufactured by Wako Pure Chemical Industries, Ltd.) prepared in a concentration of 0.5 mg/ml was applied to the membrane at a position of 12 mm from the bottom, thereby forming a line shape. The thus coated membrane was dried at 50° C. for 30 minutes with a hot-air dryer. Thereafter, the membrane was immersed in 500 ml of a blocking solution (a 50 mM borate buffer (pH 8.5) containing 0.5% casein (milk-derived product, product No. 030-01505, manufactured by Wako Pure Chemical Industries, Ltd.)) placed in a vat, and it was left at rest for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5)) placed in a similar vat, and it was then left at rest for 30 minutes. Thereafter, the membrane was taken out of the solution, and it was then dried overnight at room temperature, so as to obtain an antibody-immobilized membrane.

(1-4) Preparation of Immunochromatographic Membrane and Kit

An antibody-immobilized membrane 3 prepared in (1-3) above was attached to a back adhesive sheet 1 (ARcare9020; manufactured by NIPPN TechnoCluster, Inc.). At that time, an anti-hCG antibody line side of the membrane long sides was defined as a lower side. The gold colloid antibody-retaining pad 2 prepared in (1-2) above was attached to the lower side of the antibody-immobilized membrane, such that they were overlapped at a portion of approximately 2 mm. Thereafter, a sample-adding pad 5 (a glass fiber pad (Glass Fiber Conjugated Pad; manufactured by Millipore Corp) cut into a size of 18 mm×150 mm) was further attached to the lower side of the gold colloid antibody-retaining pad, such that they were overlapped at a portion of approximately 4 mm. Thereafter, an adsorbent pad 4 (a cellulose membrane (Cellulose Fiber Sample Pad; manufactured by Millipore Corp.) cut into a size of 20 mm×150 mm) was further attached to the upper side of the antibody-immobilized membrane, such that they were overlapped at a portion of approximately 5 mm. The long side of the thus laminated member was cut in parallel into short sections using guillotine shears (CM4000; manufactured by NIPPN TechnoCluster, Inc.), such that the cut section had a width of 5 mm, thereby producing immunochromatographic strips each having a size of 5 mm×55 mm. These immunochromatographic strips were placed in plastic cases (manufactured by NIPPN TechnoCluster, Inc.), so as to prepare an immunochromatographic kit used in a test.

(2) Test hCG (recombinant hCH R-506; manufactured by ROHTO Pharmaceutical Co., Ltd.) was dissolved in a PBS buffer containing 1% by mass of BSA to prepare an hCG solution used in a $1.8 \times 10^{-9}$M test. 100 µL of this antigen solution was added to the immunochromatographic kit prepared in (1-4) above, and it was then left at rest for 10 minutes. Thereafter, the internal membrane was taken out. The sample pad was removed, and the absorbent pad was also removed. As a new absorbent pad, a cellulose membrane (Cellulose Fiber Sample Pad; manufactured by Millipore Corp.) cut into a size of 20 mm×5 mm was attached again to a site on the membrane, at which the previous absorbent pad had been attached. As described in Example 1, two Whatman membranes (Whatman QMA) were laminated on the side upstream of the aforementioned membrane, so as to form a bifurcated portion. Pressure was given on the side downstream of the laminated portion.

1) Preparation of Solution (A) Containing Silver Component 40 mL of an aqueous solution of 1 mol/L iron nitrate prepared by dissolving iron nitrate (III) nonahydrate (manufactured by Wako Pure Chemical Industries, Ltd.; 095-00995) in water, 10.5 g of citric acid (manufactured by Wako Pure Chemical Industries, Ltd.; 038-06925), 0.1 g of dodecylamine (manufactured by Wako Pure Chemical Industries, Ltd.; 123-00246), and 0.1 g of $C_9H_{19}$—$C_6H_4$—O—$(CH_2CH_2O)_{50}$H were dissolved in 325 g of water. After all the compounds had been fully dissolved in the water, 40 mL of nitric acid (10%) was added to the mixed solution, while it was stirred with a stirrer. 80 mL of this solution was weighed, and 11.76 g of iron (II) ammonium sulfate hexahydrate (manufactured by Wako Pure Chemical Industries, Ltd.; 091-00855) was then added to the solution, thereby obtaining solution (A) containing a silver component 2) Preparation of Solution (B) Containing Reducing Agent Water was added to 10 mL of a silver nitrate solution (containing 10 g of silver nitrate) to a total amount of 100 g, thereby preparing solution (B) containing a reducing agent (a 10%-by-weight silver nitrate aqueous solution).

Comparative Example 3

Figure 8:
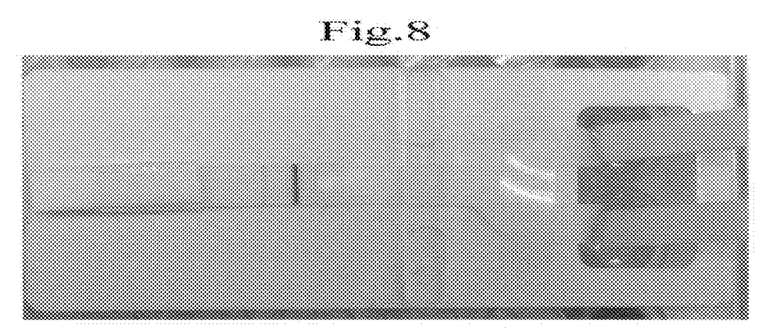
FIG. 8 shows the results of Comparative example 3.

A silver amplification solution (a solution containing a silver component) (A) was flown through the two sections of the bifurcated portion. As a result, a test line portion was not amplified at all (FIG. 8).

Comparative Example 4

Figure 9:
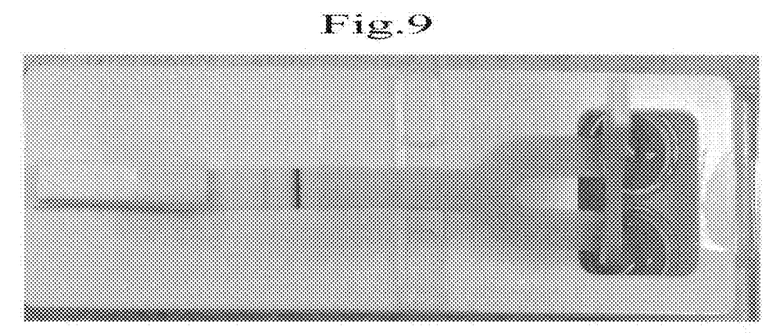
FIG. 9 shows the results of Comparative example 4.

A silver amplification solution (a solution containing a reducing agent) (B) was flown through the two sections of the bifurcated portion. As a result, a test line portion was not amplified at all (FIG. 9).

Example 2

Figure 10:
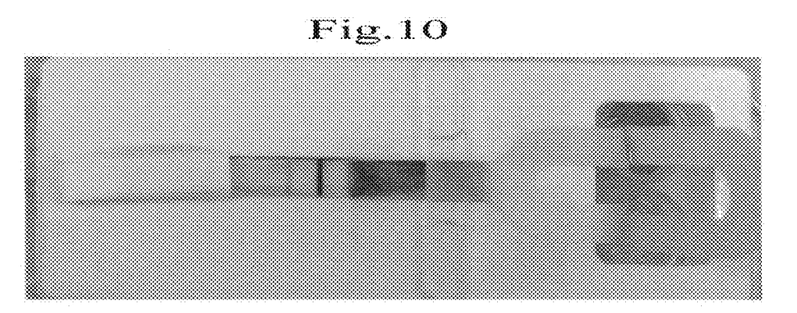

A silver amplification solution (a solution containing a silver component) (A) was flown through one section of the bifurcated portion, whereas another silver amplification solution (a solution containing a reducing agent) (B) was flown through the other section. As a result, a test line portion was amplified with silver, and it was changed to black color, so that the degree of visual observation was enhanced (FIG. 10). Since two types of solutions were mixed in a membrane, silver amplification occurred at the test line.

The invention claimed is:

1. A method for mixing two or more types of liquids in a porous carrier, which comprises:
   (a) providing a device comprising:
      a first porous carrier having an upstream portion and a downstream portion that are bent to form an integrated body;
      a second porous carrier having an upstream portion and a downstream portion that are bent to form an integrated body;
      wherein the downstream portion of the first porous carrier is laminated on the downstream portion of the second porous carrier such that their upstream portions form a bifurcated end;
   (b) adding a first liquid to the upstream portion of the first porous carrier;
   (c) adding a second liquid to the upstream portion of the second porous carrier;
   (d) applying an external force in a vertical direction so as to mix the first and second liquid together.

2. The method according to claim 1 for use in a sandwich or competitive immunoassay, which method further comprises:
   (a) a labeled first binding partner that specifically binds to a test substance;
   (b) a reaction site disposed on either the first or second porous carrier comprising an immobilized second binding partner specific to the test substance or the labeled first specific binding partner;
   (c) applying a sample suspected of containing the test substance to the first or second porous support;
   (d) causing the test substance and the labeled specific binding partner to mix, and capturing the test substance and/or the labeling substance at the reaction site
   (e) detecting the labeled specific binding partner at the reaction site and relating it to the presence or amount of the test substance.

3. The method according to claim 2 wherein the first binding substance is an antibody, and/or the second binding substance is an antibody.

4. The method according to claim 1, wherein one of the first liquid and the second liquid contains any one of silver, silver ion and silver compound, and the other of the first liquid and the second liquid contains a reducing agent.

* * * * *